(12) United States Patent
Mueller et al.

(10) Patent No.: US 10,821,015 B2
(45) Date of Patent: Nov. 3, 2020

(54) ANKLE BRACE

(71) Applicant: Mueller Sports Medicine, Inc., Prairie du Sac, WI (US)

(72) Inventors: Brett Mueller, Middleton, WI (US); Zhaodong Max Li, Lodi, WI (US)

(73) Assignee: Mueller Sports Medicine, Inc., Prairie du Sac, WI (US)

( * ) Notice: Subject to any disclaimer, the term of this patent is extended or adjusted under 35 U.S.C. 154(b) by 991 days.

(21) Appl. No.: 14/260,114

(22) Filed: Apr. 23, 2014

(65) Prior Publication Data

US 2014/0316321 A1    Oct. 23, 2014

Related U.S. Application Data

(60) Provisional application No. 61/815,118, filed on Apr. 23, 2013.

(51) Int. Cl.
 *A61F 5/01*    (2006.01)

(52) U.S. Cl.
 CPC .................. *A61F 5/0111* (2013.01)

(58) Field of Classification Search
 CPC .. A61F 5/01; A61F 5/058; A61F 13/06; A61F 5/0111; A61F 5/0585; A61F 5/0102; A61F 5/05; A61F 5/0127; A61F 5/0113; A61F 5/0195; A61F 5/37; A61F 13/00; A61F 13/066; A61H 1/0266
 USPC ........ 602/27, 65, 5, 23, 60, 28, 62; 128/869, 128/882, 846; 601/27–28
 See application file for complete search history.

(56) References Cited

U.S. PATENT DOCUMENTS

| | | | | |
|---|---|---|---|---|
| 3,506,000 A * | 4/1970 | Baker | ................ | A61F 13/066 2/22 |
| 3,680,551 A * | 8/1972 | Bell | ................ | A61F 5/04 602/36 |
| 4,878,504 A * | 11/1989 | Nelson | ................ | A61F 13/066 602/27 |
| 5,472,414 A * | 12/1995 | Detty | ................ | A61F 5/0111 128/871 |
| 5,906,206 A * | 5/1999 | Shaw | ................ | A61F 5/0104 128/882 |
| 6,663,583 B1 * | 12/2003 | Janis | ................ | A61F 5/0111 602/65 |
| 8,721,578 B2 * | 5/2014 | Gaylord | ................ | A61F 5/0102 602/65 |
| 2005/0288615 A1 * | 12/2005 | Gaylord | ................ | A61F 5/0111 602/65 |
| 2009/0112140 A1 * | 4/2009 | Gaylord | ................ | A61F 5/0111 602/27 |

* cited by examiner

*Primary Examiner* — Rachael E Bredefeld
*Assistant Examiner* — Caitlin A Carreiro
(74) *Attorney, Agent, or Firm* — Rick L. Abegglen

(57) ABSTRACT

A ankle brace for use by athletes or others requiring protection and support of the ankle. The ankle brace includes a base and a tension member. The base is made of elastic material and configured to closely fit around portions of the ankle and adjacent foot and leg portions. A tensioning member is fastened to the interior surface of the base, with the tensioning straps extending through apertures in the base for detachable attachment to the exterior surface of the base.

23 Claims, 9 Drawing Sheets

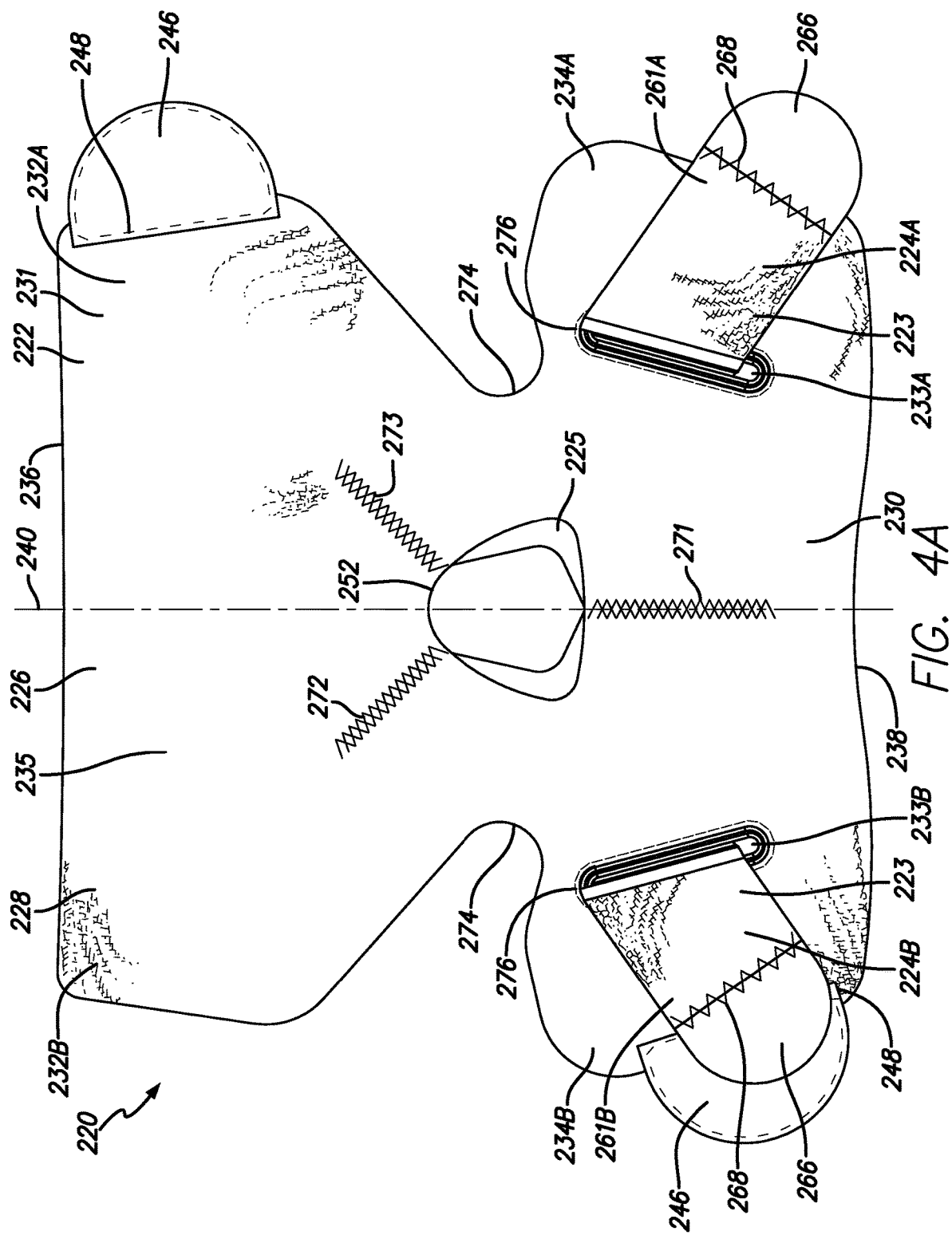

ANKLE BRACE

CROSS REFERENCE TO RELATED APPLICATIONS

This application claims priority to provisional application No. 61/815,118 filed Apr. 23, 2013, the disclosure of which is incorporated by reference.

FIELD OF THE INVENTION

This invention relates generally to the field of articles worn by persons to reduce the likelihood, severity, or exacerbation of injury to the body, and more specifically to the field of braces worn on the ankle.

BACKGROUND OF THE INVENTION

Flexible ankle braces are used by athletes and other persons engaged in vigorous physical activity to protect the ankle from injury and to avoid exacerbation of existing injury. The ankle is one of the most heavily used joints of the body, as it is used in any activity that involves walking or running. The ankle is also a common subject of injury, due to the relatively high levels of stress it must bear. During normal ambulation, in occupations involving physical labor, and especially during strenuous sports, the ankle can undergo abnormal motions as a result of quick changes in direction, fatigue, uneven surfaces, or impacts. These abnormal motions can cause sprains or more serious injuries, including dislocation, stretching, or tearing of the tissues that make up the ankle.

Devices to protect the ankle against abnormal motions have been used for many years, in a variety of specific embodiments which vary in their abilities to protect against the different types of abnormal motions such as the ankle brace discussed in U.S. Pat. No. 5,472,414. However, the protections afforded by these devices against abnormal motion are often accompanied by a reduction in range or ease of normal motion, and may be accompanied by other undesirable aspects such as poor performance, added weight, difficulty of application, fit inside footwear, cost, and/or appearance.

For these reasons, there has long been motivation to find an improved ankle brace which can protect the ankle from abnormal motions without affecting the range or ease of normal motion, while avoiding the undesirable aspects of prior art devices.

SUMMARY OF THE INVENTION

In a preferred embodiment, an ankle brace according to the present invention includes a tension member comprising a pair of tensioning straps, wherein the tension member is permanently fastened to the interior surface of the base of the ankle brace.

According to another aspect of the invention, an ankle brace according to the present invention includes a base and a tension member comprising a pair of tensioning straps, wherein the tension member is permanently fastened to the base by a plurality of stitches through the mid-line axes of the base and tension member.

According to another aspect of the invention, an ankle brace according to the present invention includes a base with a foot portion having a pair of apertures, and a tension member comprising a pair of tensioning straps and having a central portion positioned between the base and the bottom of the foot when worn, with the tensioning straps extending through the apertures in the base when the brace is worn.

Further objects, features, and advantages of the invention will be apparent from the following detailed description when taken in conjunction with the accompanying drawings.

BRIEF DESCRIPTION OF THE DRAWINGS

In the drawings:

FIG. 4A is a plan view of a second embodiment of an ankle brace according to the present invention, laid flat to expose the exterior surface of the brace;

DETAILED DESCRIPTION OF THE INVENTION

Figure 1A:
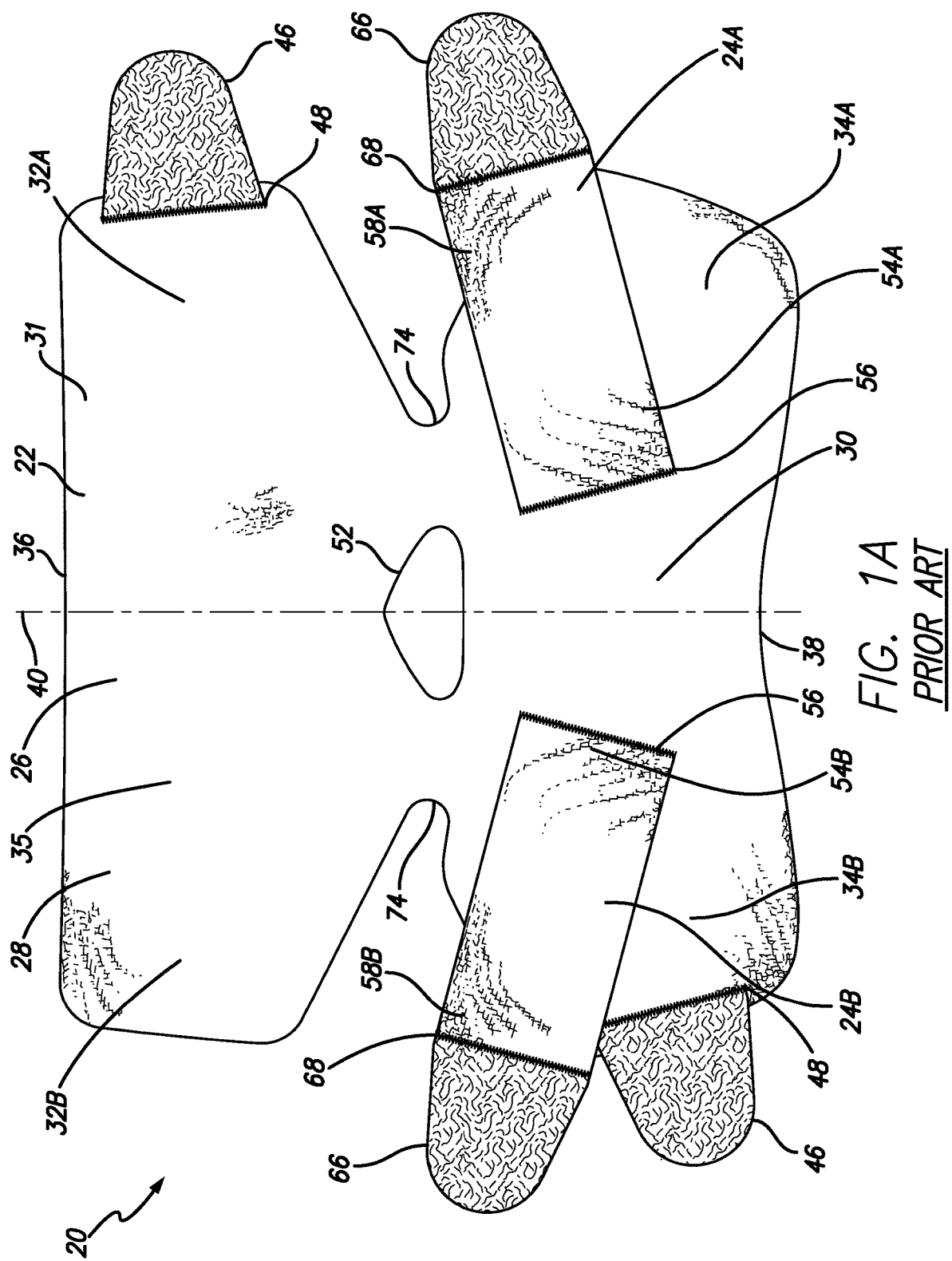
FIG. 1A is a plan view of a prior art ankle brace, laid flat to expose the exterior surface of the brace.
Figure 1B:
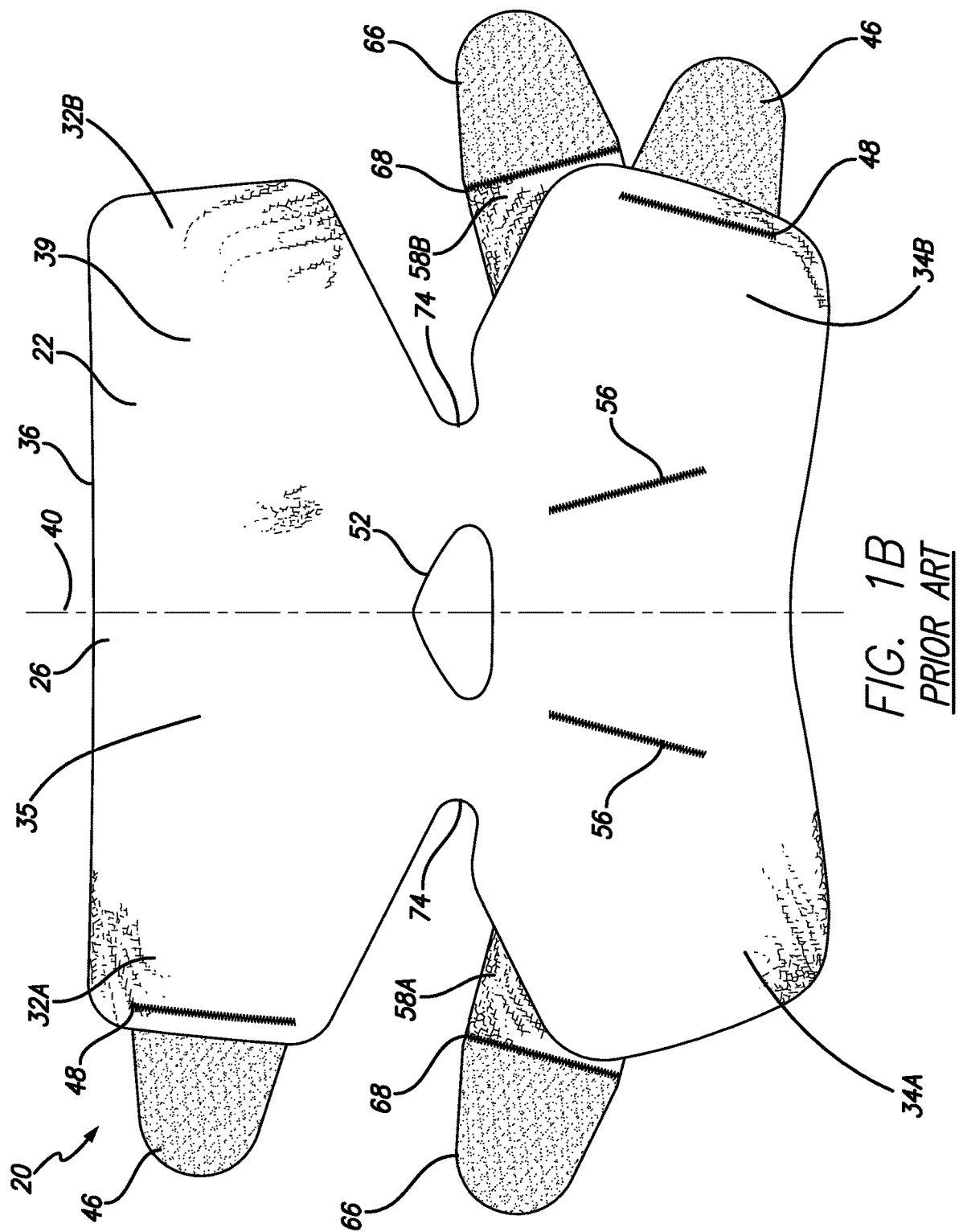
FIG. 1B is a plan view of the prior art ankle brace of FIG. 1A, laid flat to expose the interior surface of the brace.

Referring to the drawings, FIGS. 1A and 1B show a prior art ankle brace 20, similar to the design taught in U.S. Pat. No. 5,472,414, the contents of which are hereby incorporated by reference. The prior art ankle brace 20 includes a base member 22 made by cutting a planar sheet 26 of an elastomeric material into the desired shape, and tension straps 24A, 24B sewn to the base 22 by stitches 56. The exterior surface 31 of the base member 22 is preferably covered with fabric bearing fiber loops 28 of the type that adheres to hook-type material when the fiber loops and hook-type material are pressed together.

The base 22 of the prior art ankle brace 20 has a base foot portion 30 and a base leg portion 35, and extends along a mid-line axis 40 running down the middle of the base 22 from a leg edge 36 to a foot edge 38. The base 22 includes leg mounting ears 32A, 32B and foot mounting ears 34A, 34B extending from the mid-line axis 40.

As perhaps best shown in FIG. 1B which shows the interior surface 39 of the base 22, the leg mounting ear 32A and the foot mounting ear 34B terminate in hook-type strap fastening tabs 46 suitable for detachable attachment to the fabric bearing fiber loops 28 on the exterior surface 31 of the base member 22. The strap fastening tabs 46 are sewn to the mounting ears with stitches 48.

The base preferably has a heel opening 52 to receive the heel when the brace is worn and is formed to include a side recess 74 between the leg mounting ears 32A, 32B and the foot mounting ears 34A, 34B to prevent bunching when the brace is worn, although these features are not required.

As perhaps best shown in FIG. 1A which shows the exterior surface 31 of the base 22, the prior art ankle brace 20 includes tension straps 24A, 24B. The tension straps 24A, 24B have fixed ends 54A, 54B sewn to the base by stitches 56, and extend to free ends 58A, 58B that terminate in hook-type fastening tabs 66 suitable for detachable attachment to the fabric 28 on the exterior surface of the base 22 and sewn to the free ends 58A, 58B with stitches 68.

Figure 2A:
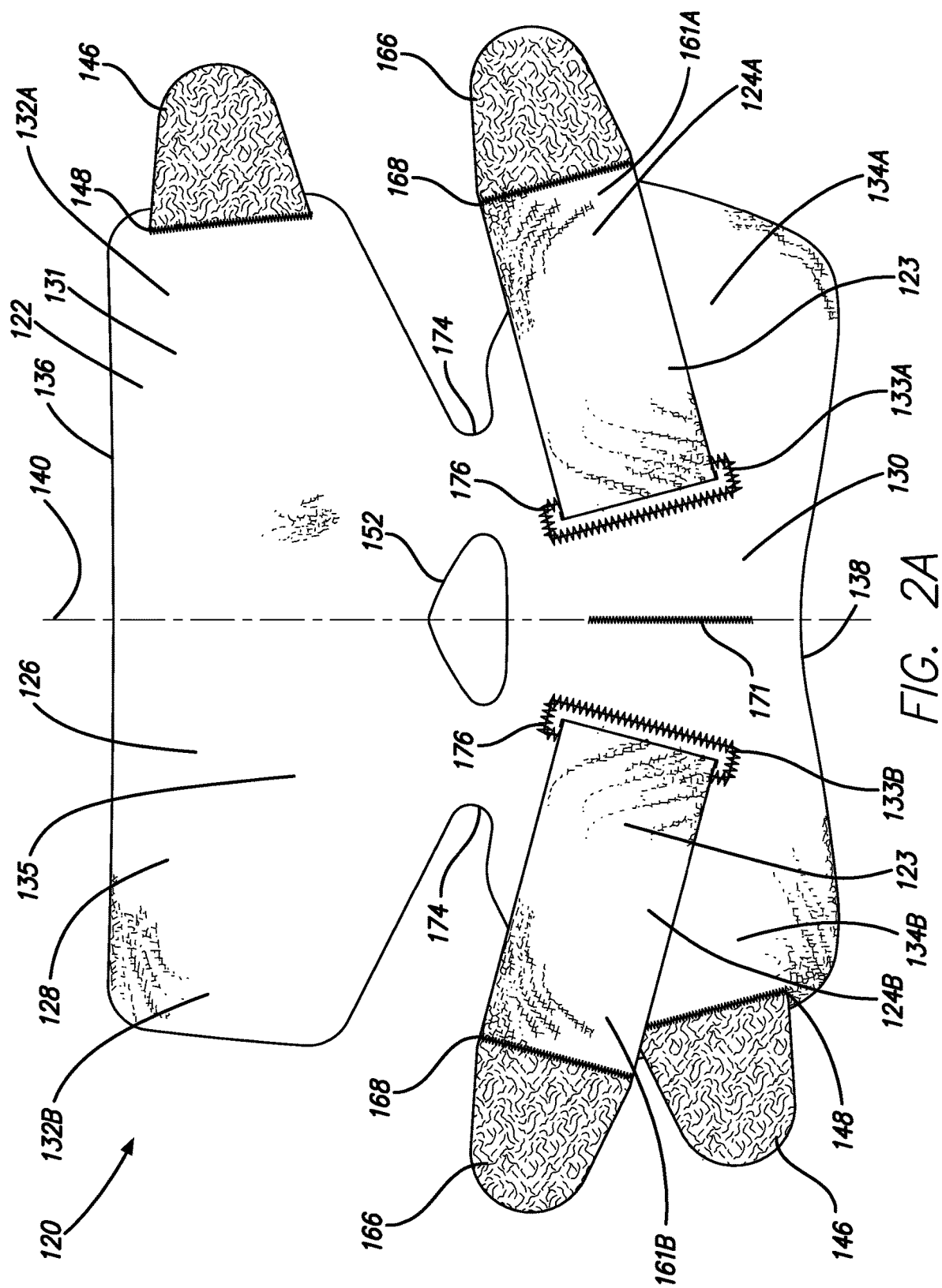
FIG. 2A is a plan view of an ankle brace according to the present invention, laid flat to expose the exterior surface of the brace.
Figure 2B:
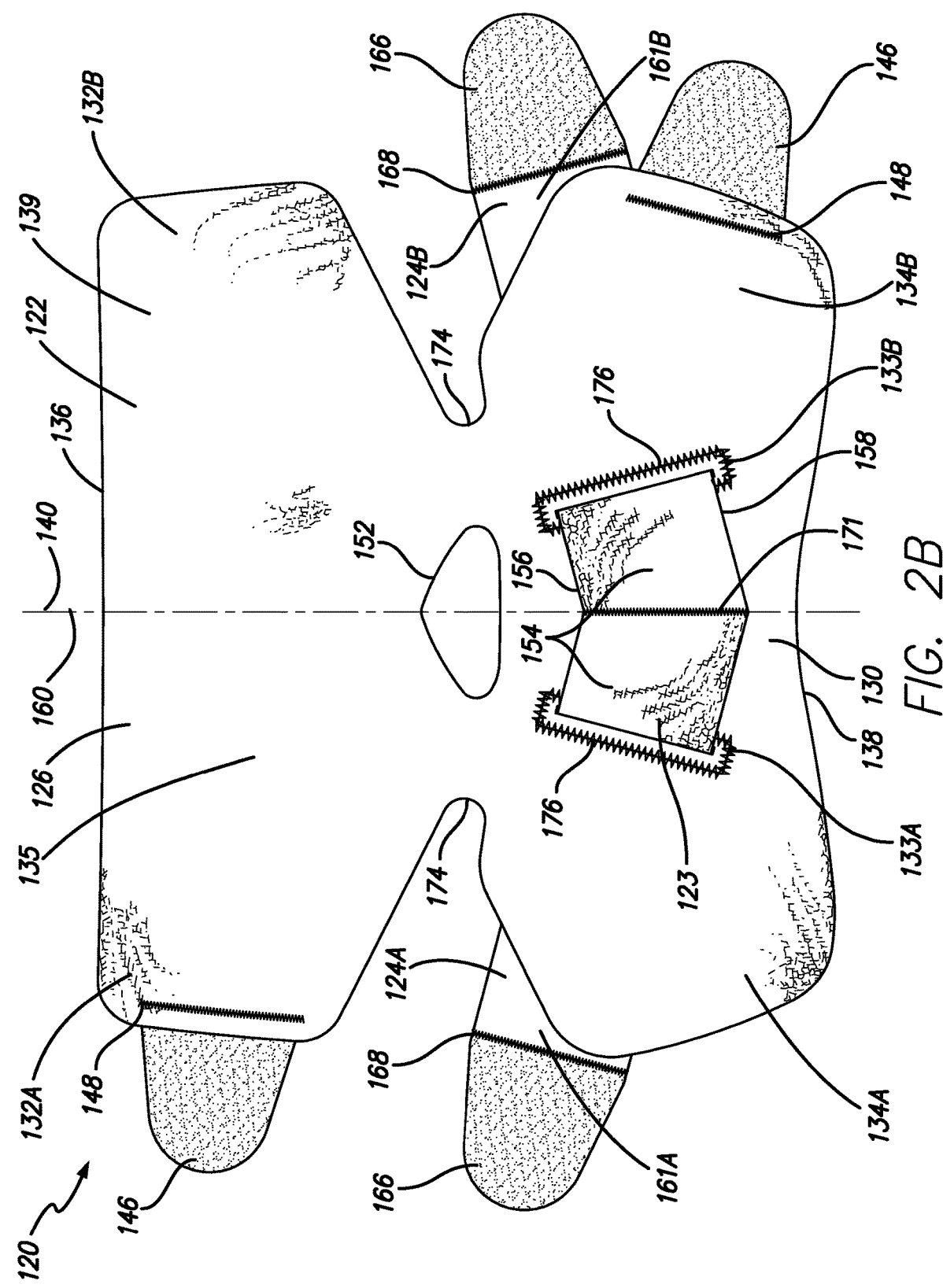
FIG. 2B is a plan view of the ankle brace of FIG. 2A, laid flat to expose the interior surface of the brace.

FIGS. 2A and 2B show exterior and interior plan views, respectively, of a ankle brace 120 according to the present invention laid flat. The ankle brace 120 includes a base member 122 made by cutting a planar sheet 126 of an elastomeric material into the desired shape, and a tension member 123 with tension member straps 124A, 124B. The exterior surface 131 of the base member 122 is preferably covered with fabric bearing fiber loops 128 of the type that adheres to hook-type material when the fiber loops and hook-type material are pressed together.

The base 122 of the ankle brace 120 has a base foot portion 130 and a base leg portion 135, and extends along a mid-line axis 140 running down the middle of the base 122 from a leg edge 136 to a foot edge 138. The base 122 includes leg mounting ears 132A, 132B and foot mounting ears 134A, 134B extending from the mid-line axis 140.

As perhaps best shown in FIG. 2B which shows the interior surface 139 of the base 122, the leg mounting ear 132A and the foot mounting ear 134B terminate in hook-type strap fastening tabs 146 suitable for detachable attachment to fabric bearing fiber loops, for example the fabric bearing loops 128 on the exterior surface 131 of the base member 122. The strap fastening tabs 146 are sewn to the mounting ears with stitches 148.

The base 122 includes apertures 133A, 133B formed as a rectangular or crescent-shaped opening in the base 122. The apertures 133, 133B may include edge binding 176.

The base preferably has a heel opening 152 to receive the heel when the brace is worn and is formed to include a side recess 174 between the leg mounting ears 132A, 132B and the foot mounting ears 134A, 134B to prevent bunching when the brace is worn, although these features are not required.

The ankle brace 120 includes a tension member 123, preferably formed of a single unitary strap of material that stretches along its length, but not across its width. The tension member 123 could also be formed of two separate straps that are sewn together. The tension member 123 has a central portion 154, an upper edge 156, a lower edge 158, and a mid-line axis 160 along its midpoint. The central portion 154 of the tension member 123 is permanently attached to the interior surface 139 of the base 122, for example by stitches 171 that extend along the mid-line axis 160, to form tension straps 124A, 124B having free ends 161A, 161B. The exterior surfaces of the tension member straps 124A, 124B are preferably covered with fabric bearing fiber loops 128 of the type that adheres to hook-type material when the fiber loops and hook-type material are pressed together.

The tension straps 124A, 124B extend through apertures 133A, 133B and terminate in hook-type fastening tabs 166 sewn to the tensioning straps with stitches 168 and suitable for detachable attachment to fabric bearing fiber loops. While the interior surfaces of the fastening tabs are covered with hook-type material, the exterior surfaces of the fastening tabs 166 are preferably covered with fabric bearing fiber loops 128 of the type that adheres to hook-type material when the fiber loops and hook-type material are pressed together.

By placing loop-type material on the exterior surface 131 of the base, on the exterior surfaces of the tension member straps 124A, 124B, and on the exterior surfaces of the fastening tabs 166, the free ends 161A, 161B of the tension member straps 124A, 124B can be attached to any of these structures (base, tension straps, or fastening tabs) by pressing the hook-type material on the inside of the fastening tabs onto any of these three structures and they will stick and lay down flat.

Figure 3A:
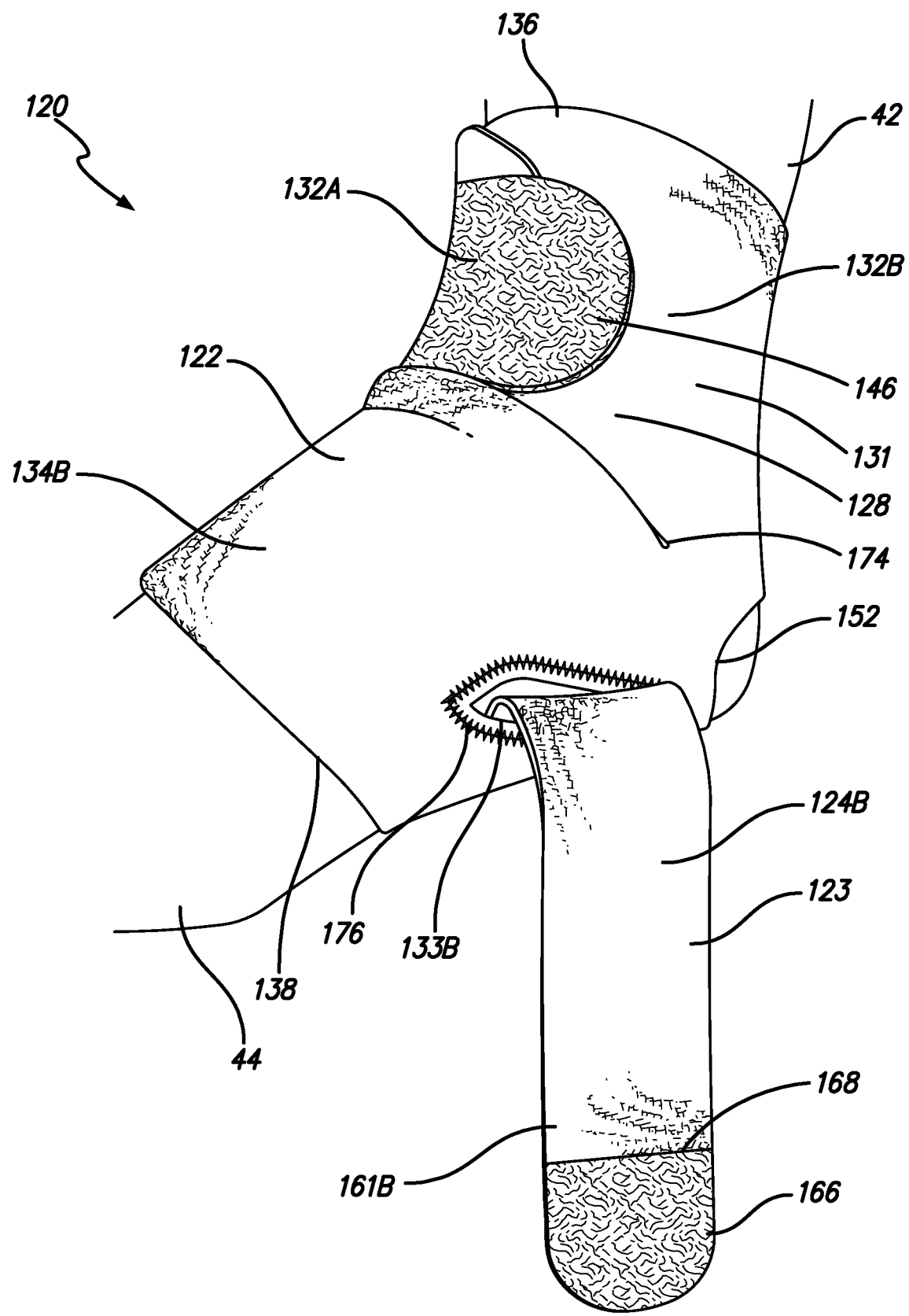
FIG. 3A is a front side view of the ankle brace of FIGS. 2A-2B, applied to the foot and lower leg with the base leg mounting straps and base foot mounting straps fastened, and with the tension member unfastened.
Figure 3B:
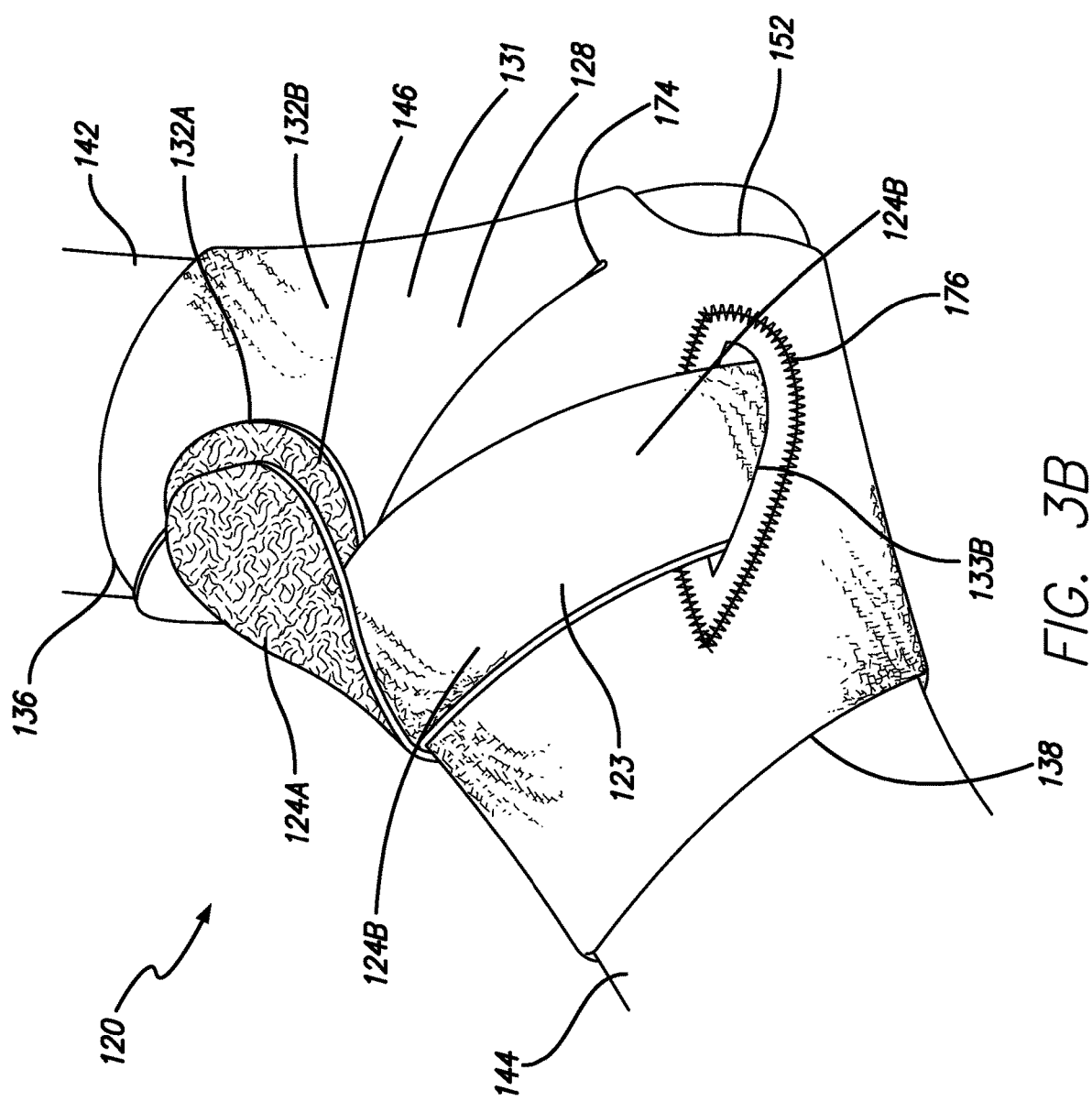
FIG. 3B is a front side view of the ankle brace of FIG. 3A, with the tension member fastened

As shown in FIG. 3A, the ankle brace 120 is worn with the foot 144 extending from the foot edge 138 of the base 122 and with the leg 142 extending from the leg edge 136 of the base 122. The base 122 is first applied to the foot with the foot mounting ears 134A and 134B wrapped to overlap, with the hook-type fastening tabs 146 at the end of the foot mounting ear 134B pressed together to adhere with the fabric bearing fiber loops 128 on the exterior surface of the foot mounting ear 134A in order to fasten the foot portion 130 about the foot 144 of the wearer. Then the leg mounting ears 132A, 12B are wrapped to overlap around the lower leg 42, and pressed together to adhere in a similar fashion to fasten the leg portion 135 about the leg 142 of the wearer. Finally, as shown in FIG. 3B, the tension straps 124A and 124B are wrapped to overlap around the front of the foot with the hook-type fastening tabs 166 adhering to the fabric bearing fiber loops 128 on the surface of the tension straps 124A, 124B and/or on the surface of the base 122 and/or on the external surface of the fastening tabs 166.

While there are some similarities between the prior art ankle brace 20 and a ankle brace 120 according to the present invention, there are (without limitation) at least three important differences. These differences in structure are believed to enhance and concentrate the support and "pull" provided by the tension member. This beneficial effect may be enhanced if the tension member is formed as a unitary structure.

First, the tension straps 24A, 24B of the prior art ankle brace 20 have fixed ends fastened at two separate points on the exterior surface 31 of the base 22. In contrast, the tension member 123 of the ankle brace 120 according to the present invention is fastened at a single point on the interior surface 139 of the base 122.

Second, the tension straps 24A, 24B of the prior art ankle brace 20 are two separate structures, so that tension in strap 24A is coupled to strap 24B through the stitches 56 and base foot portion 30. In contrast, the tension member 123 of the ankle brace 120 comprises two straps 124A, 124B either joined together or formed as a unitary structure, so that tension in strap 124A is coupled directly to strap 124B.

Third, the entire length of the tension straps 24A, 24B of the prior art ankle brace 20 are on the exterior surface 31 of the base 22 during normal use. In contrast, in the ankle brace 120 the central portion 154 of the tension member 123 lies on the interior surface 139 of the base 122, and the tension straps 124A, 124B extend through apertures 133A, 133B so that only the free ends 161A, 161B lie on the exterior surface 131 of the base 122. This allows the bottom portion of the ankle brace 120 to be smoother than if the central portion 154 of the tension member 123 was on the exterior surface, to enhance the fit of the brace in footwear.

Figure 4B:
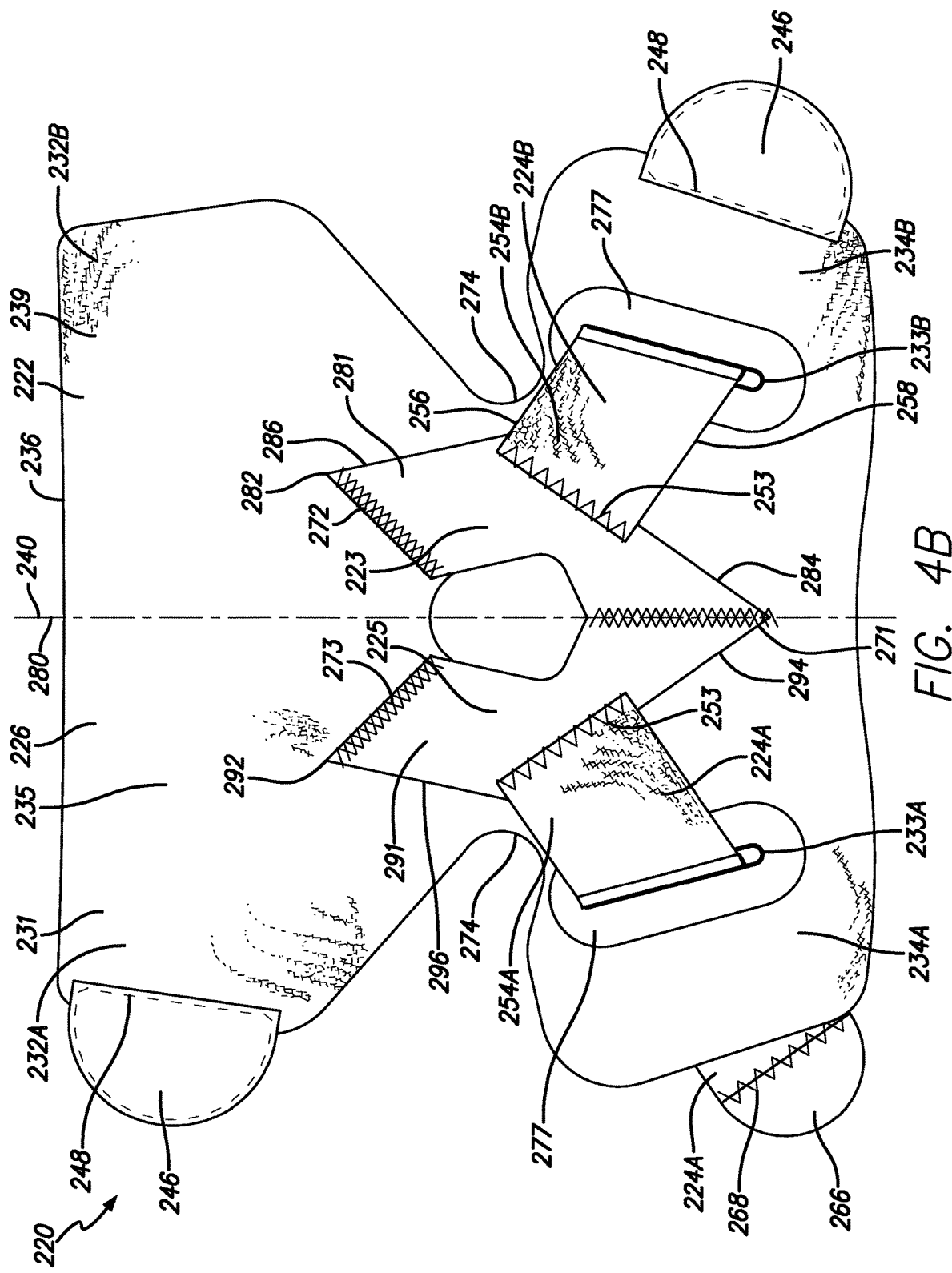
FIG. 4B is a plan view of the ankle brace of FIG. 4A, laid flat to expose the interior surface of the brace.

FIGS. 4A and 4B show exterior and interior plan views, respectively, of a second embodiment of an ankle brace 220 according to the present invention laid flat. The ankle brace 220 is similar to the ankle brace 120, with a base member 222 made by cutting a planar sheet 226 of an elastomeric material (such as a coated polyurethane foam) into the desired shape, and is applied to the foot in a similar fashion.

However, the ankle brace 220 includes a different tension member 223 comprising tension member strap portions 224A, 224B and an anchor portion 225 permanently fastened to the base member, for example by stitching. The ankle brace 220 also includes aperture reinforcements (eyelets) 276.

The base 222 of the ankle brace 220 also has a base foot portion 230 and a base leg portion 235, and extends along a mid-line axis 240 running down the middle of the base 222 from a leg edge 236 to a foot edge 238. The base 222 includes leg mounting ears 232A, 232B and foot mounting ears 234A, 234B extending from the mid-line axis 240.

As perhaps best shown in FIG. 4B which shows the interior surface 239 of the base 222, the leg mounting ear 232A and the foot mounting ear 234B terminate in hook-type strap fastening tabs 246 suitable for detachable attachment to fabric bearing fiber loops, for example fabric bearing loops 228 on the exterior surface 231 of the base member 222. The strap fastening tabs 246 are sewn to the mounting ears with stitches 248.

Figures 6A, 6B:
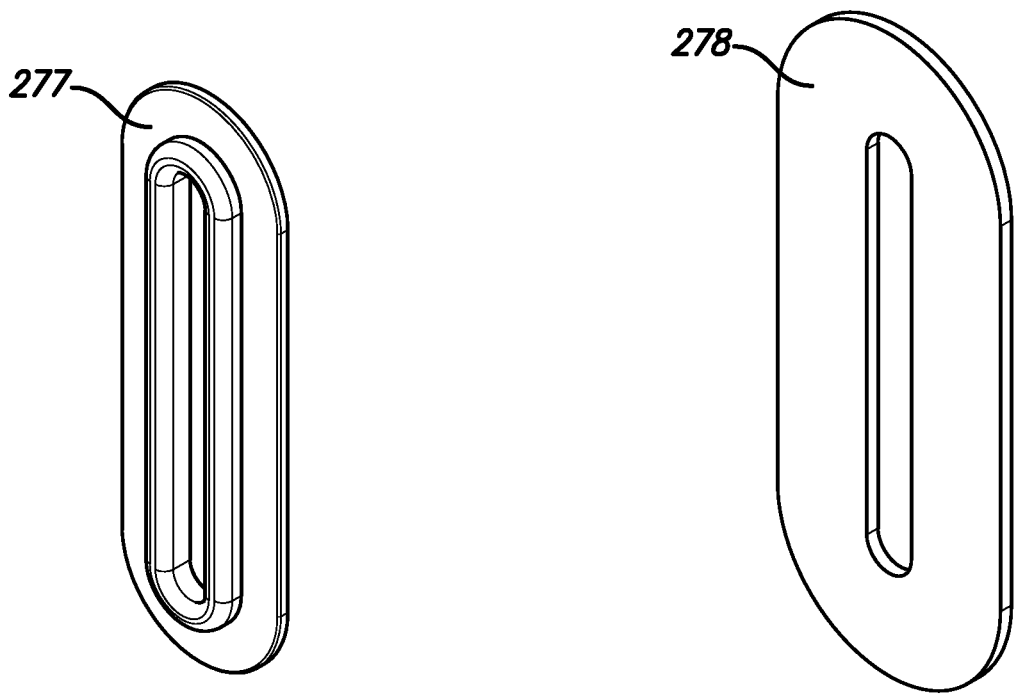
FIG. 6A is a perspective view of an aperture reinforcement base for use in the ankle brace of FIGS. 4A-4B.
FIG. 6B is a perspective view of an aperture reinforcement backing for use in the ankle brace of FIGS. 4A-4B.

The base 222 includes apertures 233A, 233B formed as openings in the base 222. The apertures 233A, 233B may include aperture reinforcements (eyelets) 276, and may be shaped like a slot with semi-circular ends, however other shapes may be used. As perhaps best shown in FIGS. 6A-6B, the aperture reinforcements may be formed of a base portion 277 and a backing portion 278.

The base preferably has a heel opening 252 to receive the heel when the brace is worn and is formed to include a side recess 274 between the leg mounting ears 232A, 232B and the foot mounting ears 234A, 234B to prevent bunching when the brace is worn, although these features are not required.

The ankle brace 220 includes a tension member 223, comprising an anchor portion 225 permanently fastened to the base 222 and to strap portions 224A, 224B that extend through the apertures 233A, 233B. The anchor portion 225 may be formed of a synthetic fiber that is relatively elastic in all directions, for example of the type known as spandex in the United States or elasthane, or sold under the trademark LYCRA®, although this is not required and other materials could be used.

The strap portions 224A, 224B can be formed of an elastomeric material that is somewhat less elastic compared to the anchor portion 225, and could be, for example, the same coated polyurethane foam material bearing fabric loops 228 used for the base 222. The material for the strap portions 224A, 224B can be elastic along the length of the straps (with little elasticity across the width of the straps), instead of being elastic in all directions like the anchor portion 225.

Figure 5:
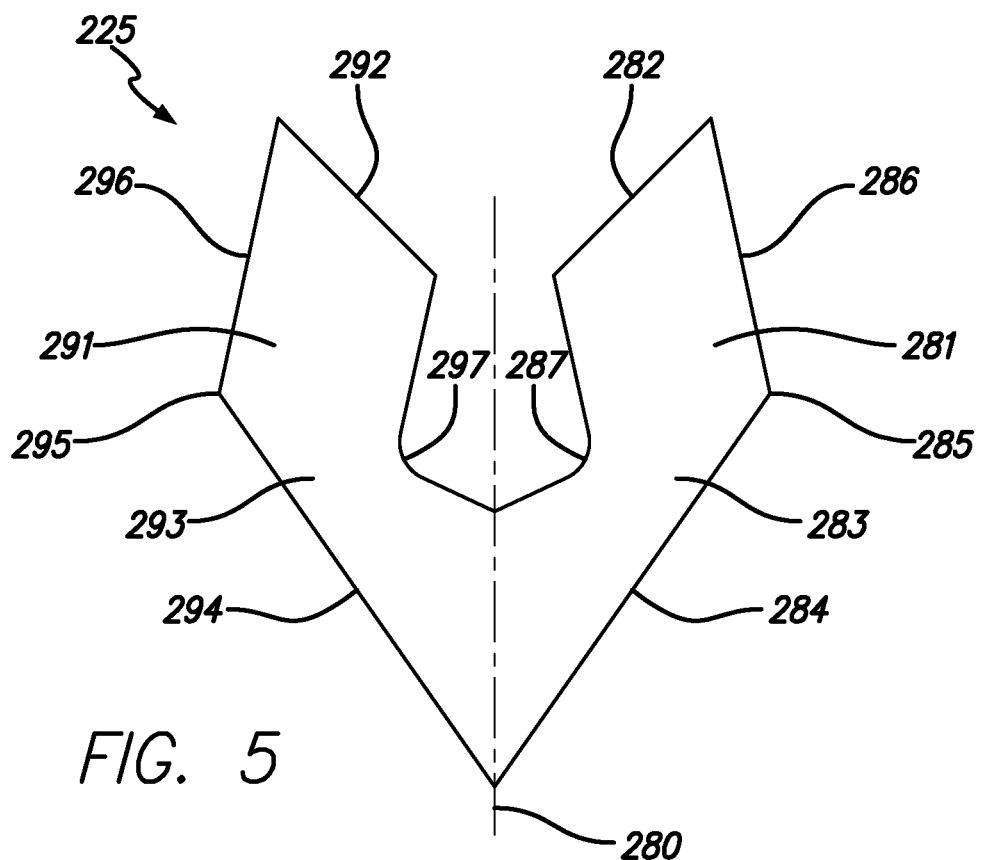
FIG. 5 is a plan view of the anchor portion of the tension member of the ankle brace of FIGS. 4A-4B.

As perhaps best shown in FIG. 5, the anchor portion 225 can be shaped roughly like the letter V, with a centerline 280 and a first arm 281 and second arm 291 forming the V with a gap between the arms. The first arm 281 extends from the centerline 280, with a middle portion 283, a first segment 284, an outer vertex 285, a second segment 286, an inner vertex 287, and an end 282. The second arm 291 also extends from the centerline 280, with a middle portion 293, a first segment 294, an outer vertex 295, a second segment 296, an inner vertex 297, and an end 292.

As perhaps best shown in FIG. 4B, the tension member anchor portion 225 is permanently fastened to the interior surface 239 of the base 222 with stitches, preferably with center stitches 271 along the centerline 280, first end stitches 272 at the end 282 of the first arm 281, and second end stitches 273 at the end 292 of the second arm 291. However, this is not required and the anchor portion 225 can be permanently fastened to the base 222 at a fewer or a greater number of locations, or at different locations.

As perhaps best shown in FIGS. 4A-4B, the tension member strap portions 224A, 224B have anchor ends 254A, 254B, upper edges 256, lower edges 258, and extend to free ends 261A, 261B. The anchor end 254A of the strap portion 224A is permanently fastened to the second arm 291 of the anchor portion 225, preferably by stitches 253 to the second arm first segment 294. The anchor end 254B of the strap portion 224B is permanently fastened to the first arm 281 of the anchor portion 225, preferably by stitches 253 to the first arm first segment 284.

The tension member strap portions 224A, 224B extend through apertures 233A, 233B and terminate in hook-type fastening tabs 266 sewn to the tensioning straps with stitches 268 and suitable for detachable attachment to fabric bearing fiber loops. While the interior surfaces of the fastening tabs are covered with hook-type material, the exterior surfaces of the fastening tabs 266 are preferably covered with fabric bearing fiber loops 228 of the type that adheres to hook-type material when the fiber loops and hook-type material are pressed together.

By placing loop-type material on the exterior surface 231 of the base, on the exterior surfaces of the tension member straps 224A, 224B, and on the exterior surfaces of the fastening tabs 266, the free ends 261A, 261B of the tension member strap portions 224A, 224B can be attached to any of these structures (base, tension strap portions, or fastening tabs) by pressing the hook-type material on the inside of the fastening tabs onto any of these three structures and they will stick and lay down flat.

There are various possibilities with regard to alternative embodiments of a ankle brace according to the invention.

Although in a preferred embodiment the ankle brace includes a base which is formed as a reclosable sleeve made from a sheet of elastic material, this is not required. The elastic material could be a single material, it could be woven or no-woven, it could be a coated material, or a sandwich of materials. The base may also be formed of a tubular elastic sleeve shaped to fit snugly about the ankle and adjacent leg portions. The base does not need to include a heel opening, and the heel opening, if present, could have a variety of shapes, e.g. circular, square, rectangular, elliptical, diamond, trapezoidal, or any substantial equivalent. All such alternative embodiments will be referred to herein as a base.

Although in a preferred embodiment the lateral sides fof the base each terminate in foot and leg mounting ears, with a side recess between the mounting ears, this particular shape is not required and a greater or lesser number of mounting ears could be used.

Although in a preferred embodiment the base is detachably fastened about the foot and leg of the wearer using mounting ears with hook and loop material of the type which adheres when pressed together, this is not required. For example, other fasteners such as buttons, clasps, buckles, pins, zippers, straps, buttons, laces, or other substantial equivalents may be substituted for the hook and loop type fastener material.

Although in a preferred embodiment, various components are permanently fastened together using stitches, this is not required. For example, other means such as glue, thermal bonding, ultrasonic bonding, or other substantial equivalents could be used.

One or more upright support members may be provided on one side, or on both sides, of the base of the ankle brace, to provide support and protect the ankle against abnormal motions, although this is not required. The upright support members may be formed, for example, by placing a resilient stay member in an elongated side pocket. The resilient stay members may be comprised of plastic, graphite, or a flattened spiral core of stainless steel or other flexible material of conventional construction commonly used in various types of braces, and may be curved to fit around the ankle.

The elongate side pocket may be formed, for example, between vertical sewn seams that fix a side pocket cover strip to the base. The side pocket cover strip may be made of the same elastic sheet material as the base, although this is not necessary. Edge binding may be fastened to the edges of the side pocket cover strips, although this is not necessary.

The exact number, location, and construction of the upright support members may vary if provided. For example, there may be a single elongated side pocket forming only one upright support member, or there may be one or more elongated side pockets on each side of the ankle with a resilient stay in each elongated side pocket. The elongated side pockets may be openable at one end to allow removal of the resilient stays, so that the brace may be washed or so that different resilient stays may be inserted to adjust the amount and type of support provided. The upright support members may include mechanical hinges, plastic rods, metal rods, narrow strips of reinforcing sheet material, or other substantial equivalents, or a combination of these various alternatives.

It is understood that the invention is not confined to the embodiments set forth herein as illustrative, but embraces all such forms thereof that come within the scope of the following claims.

What is claimed is:

1. An ankle brace, comprising:
   (a) a base formed of elastic sheet material and wearable in snug covering relationship to portions of an ankle and adjacent portions of a lower leg and a foot of a person, the base comprising:
   an exterior surface and an interior surface when worn;
   a base leg portion configured to wrap around the lower leg of the person, wherein the base leg portion extends from a leg edge defining a top outer edge of the base to a heel opening;
   a base foot portion configured to wrap around the foot of the person, wherein the base foot portion extends from the heel opening to a foot edge defining a bottom outer edge of the base;
   a first aperture located in the base foot portion and a second aperture located in the base foot portion; and
   a mid-line axis that extends down a center of the base in a vertical direction from the leg edge to the foot edge of the base; and
   (b) a tension member having an anchor portion wherein the anchor portion is formed as a V-shaped structure with a centerline and wherein the anchor portion is formed of elastic material and is permanently fastened at the centerline to the interior surface of the base at the mid-line axis of the base; and
   (c) a first strap portion permanently fastened to the anchor portion, and a second strap portion permanently fastened to the anchor portion, wherein the first strap portion extends through the first aperture and the second strap portion extends through the second aperture when the brace is worn.

2. The ankle brace of claim 1 wherein the anchor portion has a first arm extending from the centerline and having a first arm end permanently fastened to the base, and a second arm extending from the centerline and having a second arm end permanently fastened to the base.

3. The ankle brace of claim 2 wherein the tension member is permanently fastened to the base only along the mid-line axis.

4. The ankle brace of claim 1 wherein the anchor portion has a first arm extending from the centerline and having a first arm middle portion, and a second arm extending from the centerline and having a second arm middle portion, wherein the first strap portion is permanently fastened to the first arm middle portion, and wherein the second strap portion is permanently fastened to the second arm middle portion.

5. The ankle brace of claim 1 wherein the elastic material of the anchor portion stretches in at least two directions and wherein at least one of the first strap portion and the second strap portion is formed of a material which stretches primarily lengthwise.

6. An ankle brace, comprising:
   (a) a base formed of elastic sheet material and wearable in snug covering relationship to portions of an ankle and adjacent portions of a lower leg and a foot of a person, the base comprising:
   an exterior surface and an interior surface when worn;
   a base leg portion configured to wrap around the lower leg of the person, wherein the base leg portion extends from a leg edge defining a top outer edge of the base to a heel opening;
   a base foot portion configured to wrap around the foot of the person, wherein the base foot portion extends from the heel opening to a foot edge defining a bottom outer edge of the base;
   a first aperture located in the base foot portion and a second aperture located in the base foot portion; and
   a mid-line axis that extends down a center of the base in a vertical direction from the leg edge to the foot edge of the base; and
   (b) a tension member having a first tensioning strap and a second tensioning strap, wherein the first tensioning strap extends through the first aperture and the second tensioning strap extends through the second aperture when the brace is worn, and wherein the tension member is permanently fastened to the interior surface of the brace on the mid-line axis; and wherein the first and second apertures are configured to be positioned below the ankle of the person when worn.

7. The ankle brace of claim 6 wherein at least a portion of the exterior surface of the base bears loop-type material, and wherein the first tensioning strap and the second tensioning strap have free ends bearing a hook-type material, whereby the free ends of the first and second tensioning straps may be detachably attached to the exterior surface of the base.

8. The ankle brace of claim 6 wherein at least a portion of the exterior surface of the base bears loop-type material, wherein at least a portion of the first tensioning strap bears loop-type material, wherein at least a portion of the second tensioning strap bears loop-type material and wherein the first tensioning strap and the second tensioning strap have free ends bearing a hook-type material, whereby the free ends of the first and second tensioning straps may be detachably attached to the exterior surface of the base or the portion of the first tensioning strap or the portion of the second tensioning strap.

9. The ankle brace of claim 6 wherein the tension member has a midpoint, and wherein the tension member is permanently fastened to the base at the midpoint.

10. The ankle brace of claim 6 wherein the tension member is formed as a unitary structure and has a midpoint, and wherein the tension member is permanently fastened to the base at the midpoint.

11. The ankle brace of claim 6 wherein the tension member is permanently fastened to the interior surface of the base only along the mid-line axis.

12. An ankle brace, comprising:
(a) a base formed of elastic sheet material and wearable in snug covering relationship to portions of an ankle and adjacent portions of a lower leg and a foot of a person, the base comprising:
an exterior surface and an interior surface when worn;
a base leg portion configured to wrap around the lower leg of the person, wherein the base leg portion extends from a leg edge defining a top outer edge of the base to a heel opening;
a base foot portion configured to wrap around the foot of the person, wherein the base foot portion extends from the heel opening to a foot edge defining a bottom outer edge of the base:
a first aperture located in the base foot portion and a second aperture located in the base foot portion; and
a mid-line axis that extends down a center of the base in a vertical direction from the leg edge to the foot edge of the base; and
(b) a tension member having a first tensioning strap and a second tensioning strap, wherein the tension member is permanently fastened to the interior surface of the base on the mid-line axis; and wherein the first and second apertures are configured as openings for the first and second tensioning straps and are configured to be positioned below the ankle of the person when worn.

13. The ankle brace of claim 12 wherein the tension member has a midpoint, and wherein the tension member is permanently fastened to the base at the midpoint.

14. The ankle brace of claim 12 wherein the tension member is formed as a unitary structure and has a midpoint, and wherein the tension member is permanently fastened to the base at the midpoint.

15. The ankle brace of claim 12 wherein the tension member is permanently fastened to the interior surface of the base only along the mid-line axis.

16. An ankle brace, comprising:
(a) a base formed of elastic sheet material and wearable in snug covering relationship to portions of an ankle and adjacent portions of a lower leg and a foot of a person, the base comprising:
an exterior surface and an interior surface when worn;
a base leg portion configured to wrap around the lower leg of the person, wherein the base leg portion extends from a leg edge defining a top outer edge of the base to a heel opening;
a base foot portion configured to wrap around the foot of the person, wherein the base foot portion extends from the heel opening to a foot edge defining a bottom outer edge of the base:
a first aperture located in the base foot portion and a second aperture located in the base foot portion; and
a midline axis that extends down a center of the base in a vertical direction from the leg edge to the foot edge of the base; and
(b) a tension member divided into a first tensioning strap and a second tensioning strap at a location where the tension member is permanently fastened to the interior surface of the base on the mid-line axis; and wherein the first and second apertures are configured as openings for the first and second tensioning straps and are configured to be positioned below the ankle of the person when worn.

17. The ankle brace of claim 16 wherein the tension member has a midpoint, and wherein the tension member is permanently fastened to the base at the midpoint.

18. The ankle brace of claim 16 wherein the tension member is formed as a unitary structure and has a midpoint, and wherein the tension member is permanently fastened to the base at the midpoint.

19. The ankle brace of claim 16 wherein the tension member is permanently fastened to the interior surface of the base only along the mid-line axis.

20. An ankle brace, comprising:
(a) a base wearable in snug covering relationship to portions of an ankle and adjacent portions of a lower leg and a foot of a person, the base comprising:
an exterior surface and an interior surface when worn;
a base leg portion configured to wrap around the lower leg of the person, wherein the base leg portion extends from a leg edge defining a top outer edge of the base to a heel opening;
a base foot portion configured to wrap around the foot of the person, wherein the base foot portion extends from the heel opening to a foot edge defining a bottom outer edge of the base; and
a mid-line axis that extends down a center of the base in a vertical direction from the leg edge to the foot edge of the base; and
(b) a tension member having an anchor portion, wherein the anchor portion is formed as a V-shaped structure with a centerline and wherein the anchor portion is formed of elastic material and is permanently fastened at the centerline to the interior surface of the base at the mid-line axis of the base; and
(c) a first strap portion permanently fastened to the anchor portion, and a second strap portion permanently fastened to the anchor portion.

21. The ankle brace of claim 20 wherein the anchor portion has a first arm extending from the centerline and having a first arm middle portion, and a second arm extending from the centerline and having a second arm middle portion, wherein the first strap portion is permanently fastened to the first arm middle portion, and wherein the second strap portion is permanently fastened to the second arm middle portion.

22. The ankle brace of claim 20 wherein the anchor portion has a first arm extending from the centerline and having a first arm end permanently fastened to the base, and a second arm extending from the centerline and having a second arm end permanently fastened to the base.

23. The ankle brace of claim 20 wherein the elastic material of the anchor portion stretches in at least two directions and wherein at least one of the first strap portion and the second strap portion is formed of a material which stretches primarily lengthwise.

* * * * *